(12) United States Patent
Corum et al.

(10) Patent No.: US 10,537,265 B2
(45) Date of Patent: Jan. 21, 2020

(54) METHOD OF OSCILLOGRAM FILTERING FOR RADIAL MRI DATA

(75) Inventors: Curtis A. Corum, Shoreview, MN (US); Djaudat S. Idiyatullin, New Brighton, MN (US); Steen Moeller, Golden Valley, MN (US); Michael G. Garwood, Medina, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 209 days.

(21) Appl. No.: 13/638,465

(22) PCT Filed: Mar. 31, 2011

(86) PCT No.: PCT/US2011/030728
§ 371 (c)(1),
(2), (4) Date: Nov. 26, 2012

(87) PCT Pub. No.: WO2011/123647
PCT Pub. Date: Oct. 6, 2011

(65) Prior Publication Data
US 2013/0085374 A1    Apr. 4, 2013

Related U.S. Application Data

(60) Provisional application No. 61/319,703, filed on Mar. 31, 2010.

(51) Int. Cl.
*A61B 5/00* (2006.01)
*A61B 5/055* (2006.01)

(52) U.S. Cl.
CPC .............. *A61B 5/055* (2013.01); *A61B 5/725* (2013.01); *A61B 5/7225* (2013.01);
(Continued)

(58) Field of Classification Search
None
See application file for complete search history.

(56) References Cited

U.S. PATENT DOCUMENTS 5,525,906 A    6/1996   Crawford et al.
6,204,663 B1   3/2001   Prammer
(Continued)

FOREIGN PATENT DOCUMENTS

JP    0124503 B2     5/1989
JP    2012522574 A   9/2012
(Continued)

OTHER PUBLICATIONS

"International Application Serial No. PCT/US2011/030728, International Search Report dated Jun. 24, 2011", 6 pgs.
(Continued)

*Primary Examiner* — Rajeev P Siripurapu
(74) *Attorney, Agent, or Firm* — Quarles & Brady LLP

(57) ABSTRACT

A system includes a data receiver, a sinogram generator, a processor, a filter module, and an output module. The data receiver is configured to receive radial ordered magnetic resonance data. The sinogram generator is configured to generate a first sinogram corresponding to a view angle as a function of a readout direction for the magnetic resonance data. The processor is configured to generate an oscillogram having an angular frequency axis. The oscillogram corresponds to a Fourier transform of the first sinogram. The filter module is configured to selectively filter a peak in a projection formed along a selected axis of the oscillogram, the peak being related to an interference signal such as an RF interference. The selected axis is orthogonal to the angular frequency axis. The output module is configured to form a second sinogram corresponding to a transform of the filtered projection.

20 Claims, 3 Drawing Sheets

(52) U.S. Cl.
CPC .......... *A61B 5/7257* (2013.01); *A61B 5/7278* (2013.01); *A61B 5/742* (2013.01)

(56) References Cited

U.S. PATENT DOCUMENTS

| | | | |
|---|---|---|---|
| 6,324,242 B1* | 11/2001 | Pan .................................... | 378/4 |
| 6,420,873 B1 | 7/2002 | Guthrie | |
| 7,991,452 B2* | 8/2011 | Mistretta et al. ............. | 600/420 |
| 8,154,294 B2* | 4/2012 | Takizawa et al. ............ | 324/318 |
| 8,472,688 B2* | 6/2013 | Samsonov et al. ........... | 382/130 |
| 8,611,981 B2* | 12/2013 | Aime et al. .................... | 600/420 |
| 2006/0079754 A1* | 4/2006 | Welch et al. .................. | 600/410 |
| 2007/0014486 A1* | 1/2007 | Schiwietz et al. ............ | 382/276 |
| 2007/0188171 A1 | 8/2007 | Garwood et al. | |
| 2008/0056549 A1* | 3/2008 | Hamill et al. ................. | 382/131 |
| 2009/0169084 A1* | 7/2009 | Li ...................... | G01R 33/4824 382/131 |
| 2012/0092010 A1 | 4/2012 | Corum et al. | |

FOREIGN PATENT DOCUMENTS

WO  WO-2009126285 A1  10/2009
WO  WO-2011123647 A1  10/2011

OTHER PUBLICATIONS

"International Application Serial No. PCT/US2011/030728, Written Opinion dated Jun. 24, 2011", 10 pgs.
Abella, M., et al., "Sinogram bow-tie filtering in FBP PET reconstruction", Medical Physics 36 (5), (Apr. 14, 2009), 1663-1671.
Bellon, Errol M., et al., "MR Artifacts: A Review", American Journal of Roentgenology, 147(6), (Dec. 1986), 1271-1281.
Carsten, Raven, "Numerical removal of ring artifacts in microtomography", Review of Scientific Instruments AIP 69 (8), (Aug. 1, 1998), 2978-2980.
Du Weiliang, et al., "Effects of constant frequency noise in magnetic resonance imaging with nonuniform k-space sampling", Medical Physics, 29 (8), (Aug. 1, 2002).
Edholm, P. R., et al., "Novel properties of the fourier decomposition of the sinogram", Proceedings of SPIE, SPIE, USA vol. 671, (Jan. 1, 1986), 8-18.
Glover, G. H, et al., "Consistent projection reconstruction (CPR) techniques for MRI.", Magn Reson Med., 29(3), (Mar. 1993), 345-51.
Happonen, A. P, et al., "Sinogram filtering using a stackgram domain", Visualization, Imaging and Image Processing, Proceedings of Theiasted International Conference, (Sep. 9, 2002), 339-343.
Lai, Ching-Ming, et al., "A gradient control device for complete three-dimensional nuclear magnetic resonance zeugmatographic imaging", Journal of Physics E: Scientific Instruments, 13, (1980), 747-750.
Monajemi, T., et al., "A bench-top megavoltage fan-beam CT using CdW04-photodiode detectors II. Image performance evaluation", Medical Physics, 33(4), (2006), 1090-1100.
Welch, EB, et al., "Self-navigated motion correction using moments of spatial projections in radial MRI", Magnetic Resonance in Medicine vol. 52, (2004), 337-345.
"German Application Serial No. 112011101171.7, Office Action dated Jun. 16, 2014", 6 pgs.
"International Application Serial No. PCT/US2011/030728, International Preliminary Report on Patentability dated Oct. 11, 2012", 10 pgs.
Zamyatin, Alexander A, et al., "Extension of the reconstruction field of view and truncation correction using sinogram decomposition", Med. Phys. 34, (2007), 1593-1604.
"Japanese Application Serial No. 2013-502845, Notice of Rejection dated Mar. 10, 2015", 7 pgs.
Idiyatullin, D., et al., "Fast and quiet MRI using a swept radiofrequency", Journal of Magnetic Resonance, 181(2), (Aug. 2006), 342-349.
"German Application Serial No. 112011101171.7, Office Action dated Nov. 26, 2014", (w/ English Translation), 6 pgs.
"German Application Serial No. 112011101171.7, Response filed Nov. 18, 2014 to Office Action dated Jun. 16, 2014", (w/ Engiish Translation of Amended Claims), 25 pgs.
"Japanese Application Serial No. 2013-502845, Argument and Amendment filed on Aug. 5, 2015 in response to Notice dated Mar. 10, 2015", (w/ English Translation of Claims), 10 pgs.
"Machine Translation of JP 01-24503B2, published on May 11, 1989", 7 pgs.

\* cited by examiner

METHOD OF OSCILLOGRAM FILTERING FOR RADIAL MRI DATA

CLAIM OF PRIORITY

This patent application is a nationalization under 35 U.S.C. 371 of PCT/US2011/030728, filed 31 Mar. 2011 and published as WO 2011/123647 on 6 Oct. 2011, which claims the benefit of priority, under 35 U.S.C. Section 119(e), to Curtis A. Corum, U.S. Provisional Patent Application Ser. No. 61/319,703, entitled "METHOD OF OSCILLOGRAM FILTERING FOR RADIAL MRI DATA," filed on Mar. 31, 2010, each of which are hereby incorporated by reference herein in their entirety.

STATEMENT REGARDING FEDERALLY SPONSORED RESEARCH OR DEVELOPMENT

This invention was made with Government support under 5P41RR008079 awarded by the National Institutes of Health. The Government has certain rights in this invention.

BACKGROUND

Artifacts in a magnetic resonance image can include intermittent and broadband noise. Current technology is inadequate to mitigate such artifacts.

BRIEF DESCRIPTION OF THE DRAWINGS

In the drawings, which are not necessarily drawn to scale, like numerals may describe similar components in different views Like numerals having different letter suffixes may represent different instances of similar components. The drawings illustrate generally, by way of example, but not by way of limitation, various embodiments discussed in the present document.

DETAILED DESCRIPTION

The following examples can be combined in any permutation or combination.

The present subject matter includes a method to filter intermittent and broadband noise from radial MRI data. The sparsity and the convexity of the radial MRI data when presented in the oscillogram domain allows filtering to separate and suppress noise (or other artifactual signals) while leaving image data minimally affected.

RF Interference and Zipper Artifacts

Radio frequency (RF) artifacts often appear in Cartesian sampled MRI images as a "zipper." The zipper artifact is generally narrow in the readout direction and elongated along the phase encode directions in the resulting image.

Figure 1:
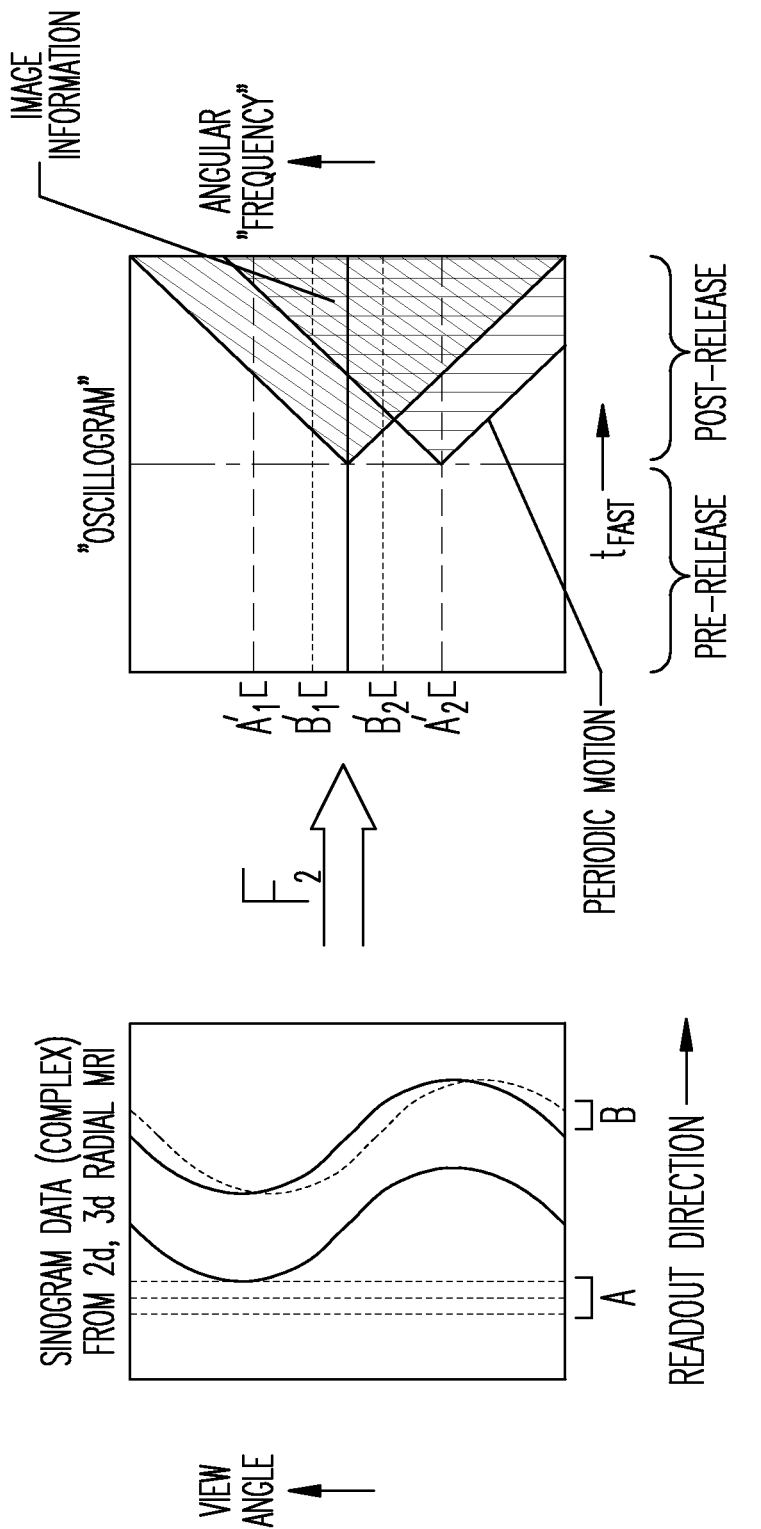
FIG. 1 illustrates a sonogram and a corresponding oscillogram.

In radial (projection) imaging, the zipper is not localized to a particular line (or a plane) in the final image, but appears in the intermediate sinogram. FIG. 1 illustrates a sinogram (sometimes referred to as a spiralogram or spirogram) having artifact A that remains constant with view angle and artifact B that appears sinusoidal with view angle.

In a 2D or 3D radial dataset, the zipper can appear as a "fan" or a "turbine" artifact with a structure depending on the view ordering as well as the frequency, bandwidth, and phase of the zipper interference.

In addition to the generally vertical (or stationary) zipper artifact, a zipper can also be moving or have a time varying frequency offset. This occurs when the field of view of the radial acquisition is offset relative to the isocenter.

In this case the RF interference may actually be at a fixed frequency but the MRI data is offset due to the frequency offset table of the off-isocenter acquisition.

A moving zipper will generally trace out a sinusoidal path that depends on the distance off-isocenter and view order. In the example shown, the base of the zipper starts at r-index B.

Other Filter Methods

A median or other filter can be applied to the vertical zipper or to a moving zipper (although the search algorithm may be time consuming).

Oscillogram

The oscillogram represents a transformed view of the sinogram. A Fourier transform is carried out along the view direction and along the readout (r-index) direction of a sinogram. In the sinogram representation, a zipper will appear as a generally vertical feature that will be moving or stationary, whereas in the oscillogram representation, the zipper will appear as a horizontal line.

According to one example of the present subject matter, the magnitude of the oscillogram can be used for filtering.

Oscillogram Filter

An example of the present subject matter is configured to automatically recognize and exclude the horizontal lines corresponding to an RF zipper artifact in the oscillogram. One method entails integrating across the horizontal axis and creating a 1D projection.

The horizontal lines of the oscillogram then transform to peaks on the projection which extend above the background.

Example

A difference image can be generated to show removal of a turbine artifact and preservation of desired image data.

In a final image, the turbine artifact appears as a zipper that is spread out by the reconstruction process into a radially symmetric pattern akin to a turbine. The structure depends on the properties of the zipper interference as well as the radial view order.

Other Applications

Periodic or nearly periodic motion is detectable as well from the oscillogram. This includes pulsitile flow, cardiac motion, and respiratory motion. Navigator-type information can be generated from the oscillogram or from a subset of the oscillogram.

FIG. 1 illustrates a zipper artifact in a sinogram produced using a SWIFT sequence.

SWIFT entails a sequence of frequency-modulated pulses with short repetition time $T_R$ that exceeds the pulse length $T_P$ by at least the amount of time needed for setting a new value (or orientation) of a magnetic field gradient used to encode spatial information. The images are processed using 3D back-projection reconstruction. In one example, frequency-modulated pulses from the hyperbolic secant family (HSn pulses) are used. In SWIFT, a shaped pulse can include N different sub-pulse elements with time-dependent amplitudes and phases. During the FM pulse, an isochromat follows the effective RF field vector until the instant resonance is attained. At resonance, the isochromat is released from the RF pulse's "hug" and thereafter almost freely precesses with a small decaying modulation, yielding spectral contamination. Thus, to extract spectral information from such a spin system response, processing is performed using a cross-correlation method similar to the method of recovering phase information in stochastic NMR. The theoretically achievable signal-to-noise ratio (SNR) per unit time for SWIFT for TR<<T1 is the same as that for pulsed FT. During SWIFT acquisition, the applied imaging gradients usually exceed all intrinsic gradients due to susceptibility or inhomogeneity. For this condition the images obtained are fully independent of transverse relaxation and signal intensity depends only on T1 and spin density. The maximum $T_1$ contrast depends on effective flip angle and the best compromise between sensitivity and contrast will have flip angles exceeding two times the Ernst angle. If flip angles are very small, $T_1$ contrast is negligible, and contrast comes entirely from spin density. Other kinds of contrast can be reached by an appropriate preparation sequence prior to or interleaved with the image acquisition.

SWIFT is but one example of a radial imaging technique and other radial imaging technology can also be used with the present subject matter.

In FIG. 1, the high intensity zipper is vertical and to the left of center at r-index A. A second zipper is also illustrated at r-index B.

The sinogram data depicted in the left panel of FIG. 1 illustrates the view angle on the vertical axis and a readout direction on the horizontal axis. The view angle data is generated sequentially and thus, the view angle can also be considered as a time axis. The sinogram data can be generated by a 2D or a 3D radial imaging protocol.

The sinogram illustrated in FIG. 1 can be viewed as a free induction decay (FID) produced by a SWIFT imaging protocol. The sinusoidal band represents the margins of the object under examination.

The zipper artifacts illustrated can have a variety of sources. For example, interference at the resonance frequency can cause such an artifact. In addition, interference from an aliased frequency or a harmonic of that frequency can also lead to a zipper artifact. Furthermore, a zipper may be caused by an RF source internal to the system or a nearby source. Zipper artifacts can also be related to an offset table.

The present subject matter includes a method and system for rectifying a sinogram using a filter. The filter can include a median filter, a notch filter, or other type of filter tailored to remove the artifact. A median filter can function in one or more dimensions and provides an output representative of a median value of the input. A median filter can reduce distortion and provide a smoothing function.

Imaging using the SWIFT protocol entails relatively fast switching and short time durations on the order of 1-4 µs. These short time durations can lead to radio frequency interference sources that can produce the zipper artifacts described herein.

As depicted in FIG. 1, the sinogram is Fourier transformed to produce an oscillogram. In the oscillogram of FIG. 1, the vertical axis (here denoted as angular frequency) can be viewed as a slow axis (time) or indexed with an arbitrary value n. The horizontal axis of the oscillogram is also a time axis and is denoted as a fast axis, here divided into a pre-release portion and a post-release portion. The data of the oscillogram represents raw k-space data in view-by-view order.

As shown in FIG. 1, interference at A in the sinogram domain transforms to $A_1'$ and $A_2'$ in the oscillogram of the figure. In addition, interference at B in the sinogram domain transforms to $B_1'$ and $B_2'$ in the oscillogram. RF interference A can be narrow or wide-band or have a constant frequency. RF interference B corresponds to a moving frequency.

Image information (non-moving) is restricted to the triangular region with diagonal cross hash marks as denoted in the figure. Periodic movement can produce displaced components as shown by the triangular region having vertical hash marks. The vertical distance between the peak of the image information triangle and the periodic motion triangle corresponds to the frequency of the interference. In addition, a broader object will result in a broader triangle in the oscillogram representation.

The present subject matter can discern between object motion and an artifact since object data will change with the view order. The interference can also be phase coherent.

Data in the sinogram is transformed by two Fourier transforms to produce the oscillogram. As noted, the vertical zipper artifact is relatively narrow in time and relatively wide in the n axis or along the frequency axis.

Figure 2:
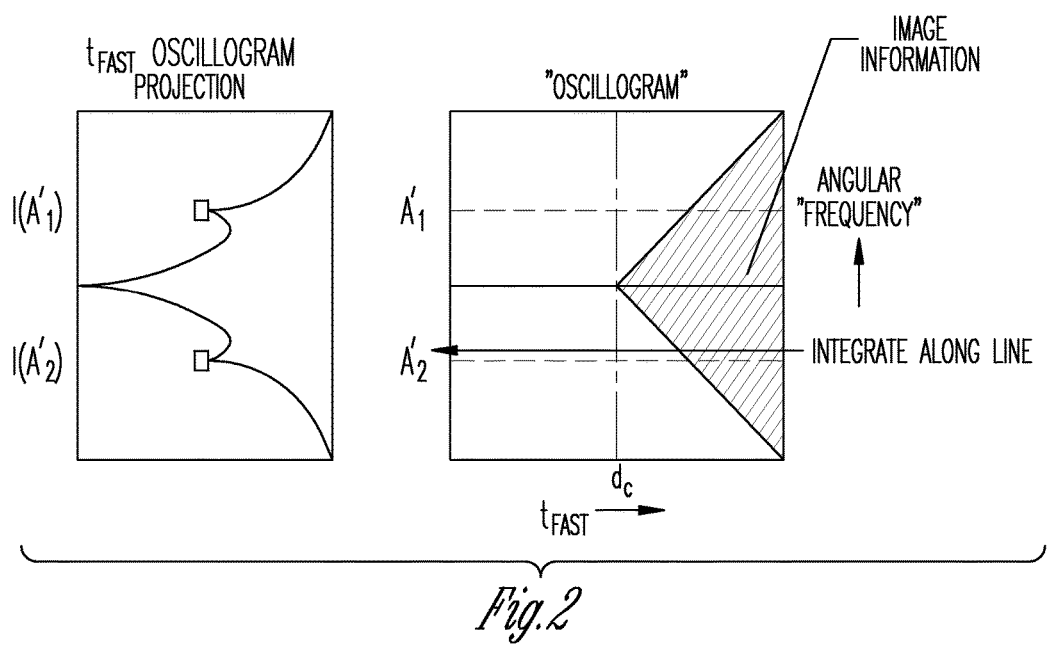
FIG. 2 illustrates an oscillogram and a corresponding projection.

FIG. 2 illustrates a 1D notch filter of the oscillogram projection along the $t_{fast}$ axis.

The projection $I(A_1')$ depicts the artifact or interference peak in the oscillogram projection and can be expressed as:

$$I(A_1') = \int_{-T}^{T} A_1' dt$$

The projection is integrated on magnitude and in one example, can be integrated on an imaginary or phase component.

The artifact extends beyond the image information and can be identified by an automatic peak finding (detection) algorithm. In FIG. 2, the rectangular boxes in the oscillogram projection denote the location.

Masking in the Oscillogram

Using the angular frequency coordinates of the RF interference, a mask-out strip is provided in the 2D oscillogram. In addition, the pre-release portion (left side) of the oscillogram can also be discarded. Masking-out entails filtering or setting to zero.

Following masking in the oscillogram projection, the image sinogram is generated by transforming and reconstructing.

In one example, a 'keep-out' zone can be established at the mid-horizontal line in the oscillogram. The keep-out zone can have a width that is user-selectable using a user-interface. In one example, the keep-out zone is approximately 10% or 5-20% around the center of the projection.

Various filters can also be used. For example, the filter can be applied to image data outside of the field of view (band-pass) or it can include an RF notch filter.

In addition, fat suppression using SWIFT can include a magnetization preparation pulse. The magnetization preparation protocol can utilize multiple notch filters on a projection. For example, multiple filters, or a comb-filter can be used with the present subject matter. A mask can be used to attenuate linear regions beyond the scope of the object.

In addition to periodic signals, motion (such as cardiac flow or respiration) can also be corrected using the present subject matter.

Figure 3:
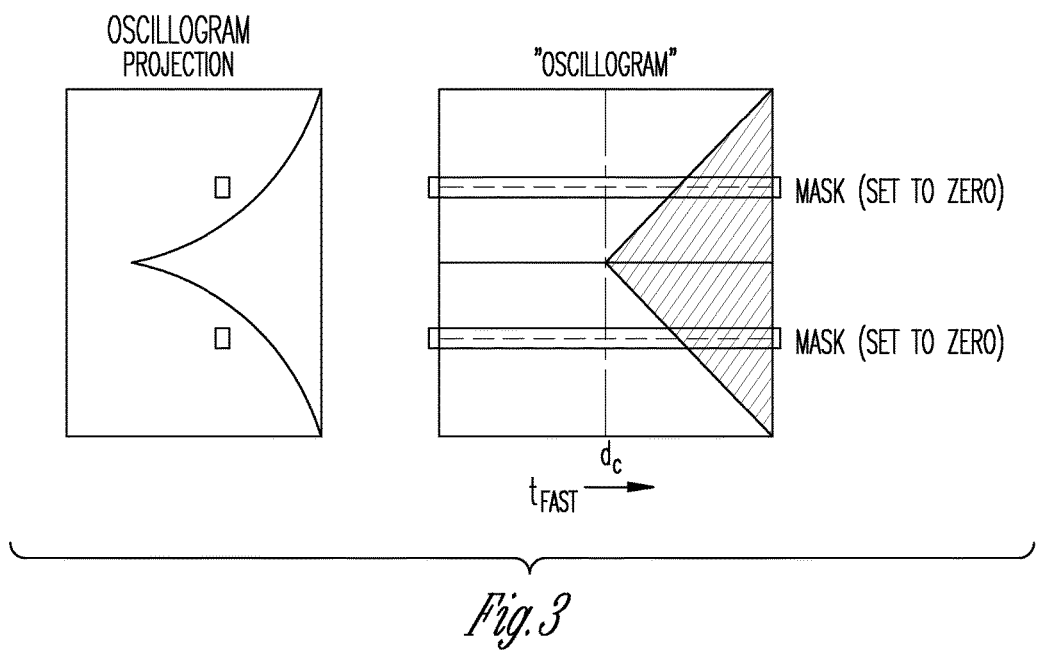
FIG. 3 illustrates an oscillogram and a corresponding projection.

FIG. 3 illustrates an oscillogram projection having mask filters configured in the oscillogram domain and tailored to remove the artifact as shown in the proceeding figures.

Figure 4:
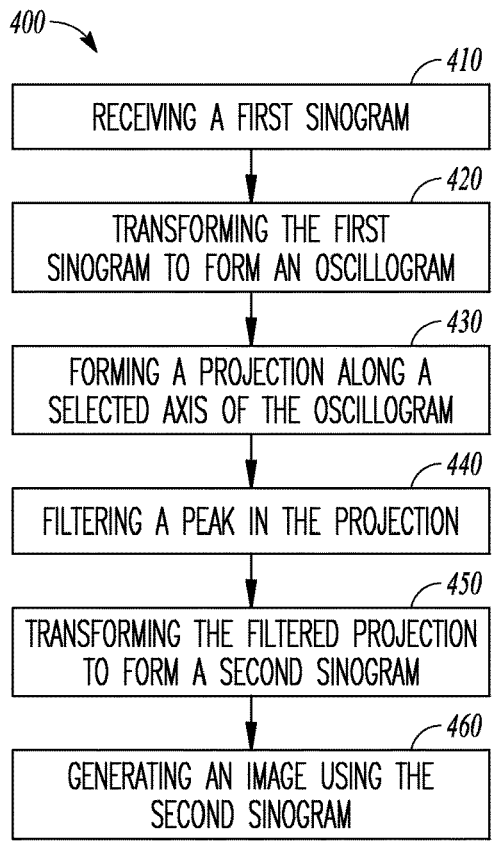
FIG. 4 illustrates a method according to one example.

FIG. 4 illustrates a flow chart of method 400 according to one example. The method includes, at 410, receiving a first sinogram corresponding to radial ordered magnetic resonance data, the first sinogram representing a view angle as a function of a readout direction for the magnetic resonance data. In addition, the method includes, at 420, transforming the first sinogram to form an oscillogram having an angular frequency axis. At 430, the method also includes forming a projection along a selected axis of the oscillogram wherein the selected axis is orthogonal to the angular frequency axis. At 440, the method includes filtering a peak in the projection and, at 450, transforming the filtered projection to form a second sinogram.

Figure 5:
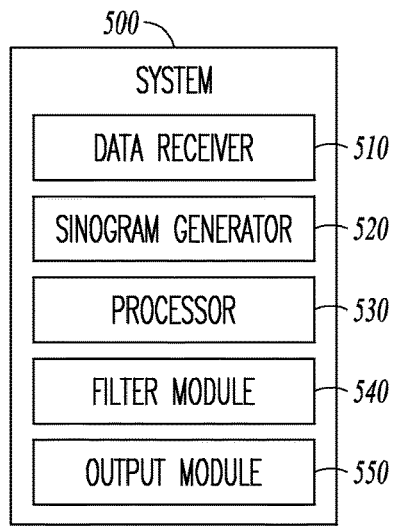
FIG. 5 includes a system according to one example.

FIG. 5 illustrates system 500 according to one example. The system can include data receiver 510, sinogram generator 520, processor 530, filter module 540, and output module 550. These elements can be discrete components or modules or integrated or combined in any combination. In addition, two or more of the elements can be combined in a single module. Data receiver 510 is configured to receive radial ordered magnetic resonance data. Sinogram generator 520 is configured to generate a first sinogram corresponding to a view angle as a function of a readout direction for the magnetic resonance data. Processor 530 is configured to generate an oscillogram having an angular frequency axis. The oscillogram corresponds to a transform of the first sinogram. Filter module 540 is configured to selectively filter a projection formed along a selected axis of the oscillogram. The selected axis is orthogonal to the angular frequency axis. Output module 550 is configured to form a second sinogram corresponding to a transform of the filtered projection. System 500 can be implemented in any combination of a computer and hardware configured as shown.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:
1. A system comprising:
   a data receiver configured to receive radial ordered magnetic resonance data, the data including an artifact and the data including phase information and frequency information;
   a sinogram generator configured to generate a first sinogram corresponding to a view angle as a function of a readout direction for the magnetic resonance data;
   a processor configured to generate an oscillogram having an angular frequency axis and a time axis that is orthogonal to the angular frequency axis, the oscillogram corresponding to a transform of the first sinogram;
   a filter module configured to selectively filter, using a peak detection algorithm to detect peaks corresponding to zipper artifacts, a projection formed along the time axis of the oscillogram that is orthogonal to the angular frequency axis; and
   an output module configured to form a second sinogram corresponding to a transform of the filtered projection and to generate an image using the second sinogram, the image having the artifact removed or suppressed.

2. The system of claim 1 wherein the data receiver is configured to receive spherical ordered data.

3. The system of claim 1 wherein the data receiver is configured to receive at least one of 2D data or 3D data.

4. The system of claim 1 wherein the processor is configured to implement at least one of a Fourier transform or an inverse Fourier transform.

5. The system of claim 1 wherein the processor is configured to implement a Fourier transform along the view angle and along the readout direction.

6. The system of claim 1 wherein the filter module is configured to form the projection by integrating magnitude components of the oscillogram.

7. The system of claim 5 wherein the filter module is configured to form a 1D projection in a direction aligned with a fast axis of the oscillogram, wherein the fast axis of the oscillogram corresponds to the Fourier transform along the readout direction of the first sinogram.

8. The system of claim 1 wherein the filter module is configured to implement at least one of a notch filter and a mask filter.

9. The system of claim 1 wherein the filter module is configured to implement a median filter.

10. The system of claim 1 wherein the filter module includes implementing a peak detector.

11. A method comprising:
receiving a first sinogram corresponding to radial ordered magnetic resonance data, the data including an artifact and the data including phase information and frequency information, the first sinogram representing a view angle as a function of a readout direction for the magnetic resonance data;
using a processor to transform the first sinogram to form an oscillogram having an angular frequency axis and a time axis that is orthogonal to the angular frequency axis;
forming a projection along the time axis of the oscillogram that is orthogonal to the angular frequency axis;
filtering a peak in the projection sing a peak detection algorithm to detect peaks corresponding to zipper artifacts;
transforming the filtered projection to form a second sinogram; and
generating an image using the second sinogram, the image having the artifact removed or suppressed.

12. The method of claim 11 wherein receiving the first sinogram corresponding to radial ordered magnetic resonance data includes receiving spherical ordered data.

13. The method of claim 11 wherein receiving the first sinogram corresponding to radial ordered magnetic resonance data includes receiving at least one of 2D data or 3D data.

14. The method of claim 11 wherein using the processor to transform includes executing at least one of a Fourier transform or an inverse Fourier transform.

15. The method of claim 11 wherein using the processor to transform the first sinogram to form an oscillogram includes executing a Fourier transform along the view angle and executing a Fourier transform along the readout direction.

16. The method of claim 11 wherein forming the projection includes forming the projection by integrating magnitude components of the oscillogram.

17. The method of claim 15 wherein forming the projection along the axis of the oscillogram includes forming a 1D projection in a direction aligned with a fast axis of the oscillogram, wherein the fast axis of the oscillogram corresponds to the Fourier transform along the readout direction of the first sinogram.

18. The method of claim 11 wherein filtering includes at least one of notch filtering or mask filtering.

19. The method of claim 11 wherein filtering includes implementing a median filter algorithm.

20. The method of claim 11 wherein filtering includes implementing a peak detection algorithm.

* * * * *

UNITED STATES PATENT AND TRADEMARK OFFICE
CERTIFICATE OF CORRECTION

PATENT NO. : 10,537,265 B2  
APPLICATION NO. : 13/638465  
DATED : January 21, 2020  
INVENTOR(S) : Curtis A. Corum et al.

It is certified that error appears in the above-identified patent and that said Letters Patent is hereby corrected as shown below:

In the Specification

Column 8, Line 1, "sing" should be --using--.

Signed and Sealed this  
Third Day of March, 2020

Andrei Iancu  
*Director of the United States Patent and Trademark Office*